United States Patent [19]
Bonnet et al.

[11] Patent Number: 5,766,228
[45] Date of Patent: Jun. 16, 1998

[54] ENSLAVED ACTIVE IMPLANTABLE MEDICAL DEVICE WITH REDUCED POWER CONSUMPTION

[75] Inventors: Jean-Luc Bonnet, Vanves; Anne Dubreuil, Boulogne, both of France

[73] Assignee: ELA Medical S.A., Montrouge, France

[21] Appl. No.: 730,735

[22] Filed: Oct. 11, 1996

[30] Foreign Application Priority Data

Oct. 13, 1995 [FR] France .................. 95 12051

[51] Int. Cl.$^6$ ............................. A61N 1/365
[52] U.S. Cl. ..................................... 607/16
[58] Field of Search .................. 607/16, 9, 17, 607/29, 28

[56] References Cited

U.S. PATENT DOCUMENTS

| | | |
|---|---|---|
| 5,014,702 | 5/1991 | Alt. |
| 5,065,759 | 11/1991 | Begemann et al.. |

FOREIGN PATENT DOCUMENTS

| | | | |
|---|---|---|---|
| 0191404A1 | 2/1986 | European Pat. Off. | A61N 1/365 |
| 0616819A3 | 2/1989 | European Pat. Off. | A61N 1/365 |
| 0431437A2 | 11/1990 | European Pat. Off. | A61N 1/378 |
| 0541338A1 | 11/1992 | European Pat. Off. | A61N 1/365 |
| 0570674A1 | 9/1993 | European Pat. Off. | A61N 1/365 |
| 0640359A2 | 8/1994 | European Pat. Off. | A61N 1/365 |
| 3939898A1 | 11/1989 | Germany | A61N 1/362 |
| 88/09684 | 12/1988 | WIPO | A61N 1/365 |

*Primary Examiner*—Scott M. Getzow
*Attorney, Agent, or Firm*—Orrick, Herrington & Sutcliffe LLP

[57] ABSTRACT

An active implantable medical device, particularly a rate responsive cardiac pacemaker having reduced power consumption. The device has a first sensor to measure a parameter that is used to control at least one function of the device, particularly a cardiac stimulation frequency, and a first sensing circuit for receiving and processing the output signals delivered by the first sensor. A switch is used to switch in and out of service the first sensing circuit according to the determined activity level of the patient bearing the device. The first sensing circuit determines a state of activity of the first sensor, this state being susceptible to take, according to predetermined criteria, a calculated value that is representative of a state of rest of the patient. The first sensing circuit is then switched according to the determined state of activity of the first sensor being established at the state of rest. Advantageously, a second sensor is used to measure a parameter representative of the activity of the patient and a second sensing circuit is used to receive and process the output signals delivered by this second sensor, such that the first sensing circuit is switched back in service as a function of the output signals delivered by the second sensor.

25 Claims, 1 Drawing Sheet

# ENSLAVED ACTIVE IMPLANTABLE MEDICAL DEVICE WITH REDUCED POWER CONSUMPTION

FIELD OF THE INVENTION

The present invention concerns an "active implantable medical device" such as those defined by the Jun. 20, 1990 directive 90/385/EEC of the European Community Council, and more particularly to cardiac pacemakers and/or defibrillators, having a function that is enslaved to, that is responsive to, a sensed parameter. Although the following description refers mainly to the case of a cardiac pacemaker, the invention also is applicable in a general manner to a great variety of electronic devices having a control function that is responsive to a sensed parameter.

BACKGROUND OF THE INVENTION

Enslaved active implantable devices are known to adapt their actions, for example, a control function, to a calculated or measured value of a parameter representative of a characteristic of the patient bearing the device. In the case of a cardiac pacemaker, the control parameter may be the stimulation frequency, which is adjusted as a function of a parameter representative of the activity or the metabolic needs (cardiac output requirements) of the patient. Many parameters, including, but not limited to, the minute ventilation, the respiratory frequency, the saturation of oxygen in the blood, the temperature, or the acceleration have been acceptably used as parameters of enslavement for control functions. In particular, these parameters have been used in the case of cardiac pacemakers, to vary the instantaneous frequency of the cardiac stimulation according to the measured or calculated parameter.

It also is envisaged, as described in U.S. Pat. No. 5,014,702, U.S. Pat. No. 5,065,759, and in U.S. application Ser. No. 08/674,261, filed Jul. 1, 1996 in the names of Jean-Luc Bonnet and Laurence Geroux, which application is co-pending, commonly assigned, and incorporated herein by reference in its entirety, to combine in some manner information from two different parameters or type of sensors, so as to profit from the advantages of each. The use of one or more sensors of enslavement contributes to the improvement of the functioning of the pacemaker by providing for the pacemaker to function in a manner that is closer to the real physiological and metabolic needs of the patient bearing the implanted device.

Nevertheless, the utilization of one or more, and more particularly several, sensors, is at the expense of an incremental energy consumption. This is due to the additional hardware circuits, the increase of which is directly associated to the enslavement parameter transducer(s) (power supply, injection of current (as in the case of minute ventilation and other sensors), production and analysis of the signal, etc.), as well as the software used to process the sensor produced signals. It is generally realized that the microprocessors or specific circuits executing the software or logic functions are typically large, energy-consuming components when they execute algorithms to process data and make decisions.

One of goals of the present invention is to reduce the global energy consumption of an active implantable medical device by seeking to operate in an intermittent manner the hardware circuits and software directly associated with sensors (elements that are hereinafter designated collectively under the name of "measure and processing circuits" or, more simply, a "sensing circuit") so as to save energy of the battery power source, and thereby to prolong as much as possible the useful life of the implanted device.

Some techniques have already been proposed in this regard. DE 39 39 898 describes to add to the device a specific supplementary sensor (an activity (acceleration) sensor), which is used to control switching in or out of service of the sensing circuit for the main sensor of enslavement according to whether or not the supplementary sensor detects an activity of the patient. However, device presents the disadvantage of adding a specific supplementary sensor having for its only object the detection of the activity. In addition to the increased complexity of the device, the supplementary sensor always is in service, that is operating. This results in an additional supplementary energy consumption such that some of the energy consumption savings obtained by turning off the main sensing circuit is lost.

WO 91/08020 describes an approach using a circuit having a phase-locked loop to control turning the only sensor on and off according to the Circadian (day and night) rhythm of the patient. A disadvantage of this device is that it takes into account only the day/night rhythm, without being able to integrate shorter periods of inactivity, for example, periods of diurnal rest.

If the disadvantage of the proposal of DE 39 39 898 is reduced based on the low energy consumption of the phase-locked loop, the configuration of the device having the phase-locked loop presents another disadvantage in that the simple nature of the prediction of the commutation, that is the switching of the unique circuit in and out of operation, does not take in account the real activity of the patient, and therefore adjusts only after variations of the day and night rhythm have occurred.

OBJECTS AND SUMMARY OF THE INVENTION

It is an object of the present invention to overcome the disadvantages associated with these earlier proposed techniques by providing an enslaved active implantable medical device, particularly a rate responsive cardiac pacemaker, that is susceptible to switch in and out of service a sensing circuit operable to determine the parameter of the sensor of enslavement, with a minimum of hardware circuits and software to achieve such switching, thereby to obtain an important energy economy, which device is also capable of taking into account activity variations of even brief duration which occur anytime in the day or night.

Broadly stated, the present invention, concerns implementing an automatic disconnection of the sensor of enslavement, independent of the specific manner in which the disconnected sensor is subsequently switched back into service. Switching the sensor, or more specifically the sensing circuits which drive the sensor and acquire and process the sensor output, out of service reduces power consumption. The sensor can be switched back into service by, for example, a second sensor as will be described below, the passing of a time period, a counter counting a selected number of events, an analysis of a detected electrocardiogram signal as performed, for example, by a software or other algorithm, or some other intrinsic command mechanism.

One aspect of the invention is directed to an improvement of a device of a kind well known in the art, as taught particularly, for example, by the aforementioned DE - 39 39 898, and which improvement comprises:

a first sensor having an output signal corresponding to a parameter that is to be used to control at least one function of the device, particularly, for example, to control a cardiac stimulation frequency;

a first sensing circuit that is responsive to the output signals delivered by the first sensor to process the output signals and determine a value of the parameter to control the function; and a switching means to switch in or out of service the first sensing circuit according to the activity of the patient bearing the device.

in which the first sensing circuit determines a state of activity of the patient. This determination may be made, for example, by comparing the first sensor output signals to predetermined criteria which is a calculated value representative of a patient state of activity, in which case the state of activity of the sensor is determined. Alternatively, the first sensor circuit may compare the parameter calculated from the first sensor output signals to a predetermined criteria which is a calculated value representative of a patient state of activity in which case the activity level of the patient is determined. In each case, the predetermined criteria is representative of a state of rest of the patient, such that it is used to discriminate a level of patient activity corresponding to rest from a level of activity corresponding to non-rest. The switching means then switches out of service the first sensing circuit according to the determined state of activity of the patient being established to correspond to a state of rest of the patient. It should be understood that switching the first sensing circuit out of service also typically results in switching out of operation the first sensor in the case that the first sensor is an active, power consuming device, powered separate from the first sensing circuit.

It also should be understood that the reference to determining the state of activity of the patient is a generic condition of which determining the state of activity of the first sensor is one species. The latter is based on the first sensor output signals as processed by the first sensing circuit relative to predetermined criteria, whereas the former is the result of the first sensing circuit processing the data and assessing the patient activity state. Each may be used with equal facility, given that an appropriate predetermined criteria is used.

Very advantageously, the device in accordance with the present invention also comprises a second sensor measuring a second parameter representative of the activity of the patient and a second sensing circuit that is responsive to the output signals delivered by the second sensor, and the switching means switches in service the first sensing circuit in response to signals delivered by the second sensor.

In one embodiment, the switching means of the device can comprise a counter, which is incremented as a function of the elapsed time after the first sensing circuit is switched out of service, such that the first sensing circuit is switched back into service according to the value reached by the counter. In this embodiment, the value reached by the counter may be physician selected, that is programmed, or an automatically adjusted value that depends on selected boundary limits and one or more historical averages of periods of activity.

In a preferred embodiment, the implanted device has two sensors. One sensor can be a sensor of effort, that is, a sensor having an output signal measuring a parameter that is preponderantly physiological in nature and delivering a signal that is a function of the effort developed by the patient. The other sensor can be a sensor of activity, that is, a sensor having an output signal measuring a parameter that is preponderantly physical in nature.

In a more preferred embodiment of the present invention having the aforementioned two sensors, the first sensor is preferably a sensor of effort operable to measure a parameter that is preponderantly physiological and delivering a signal that is a determinable function of the metabolic state of the patient, and the second sensor is a sensor of activity, and in particular an acceleration sensor having a short response time (as compared to the first sensor) operable to measure a parameter that is preponderantly physical.

BRIEF DESCRIPTION OF THE DRAWING

Other characteristics and advantages of the present invention will appear to a person of ordinary skill in the art in view of the following detailed description, made with reference to the drawing annexed that is a block diagram of a device implementing a preferred embodiment of the present invention.

DETAILED DESCRIPTION OF THE INVENTION

Figure 1:
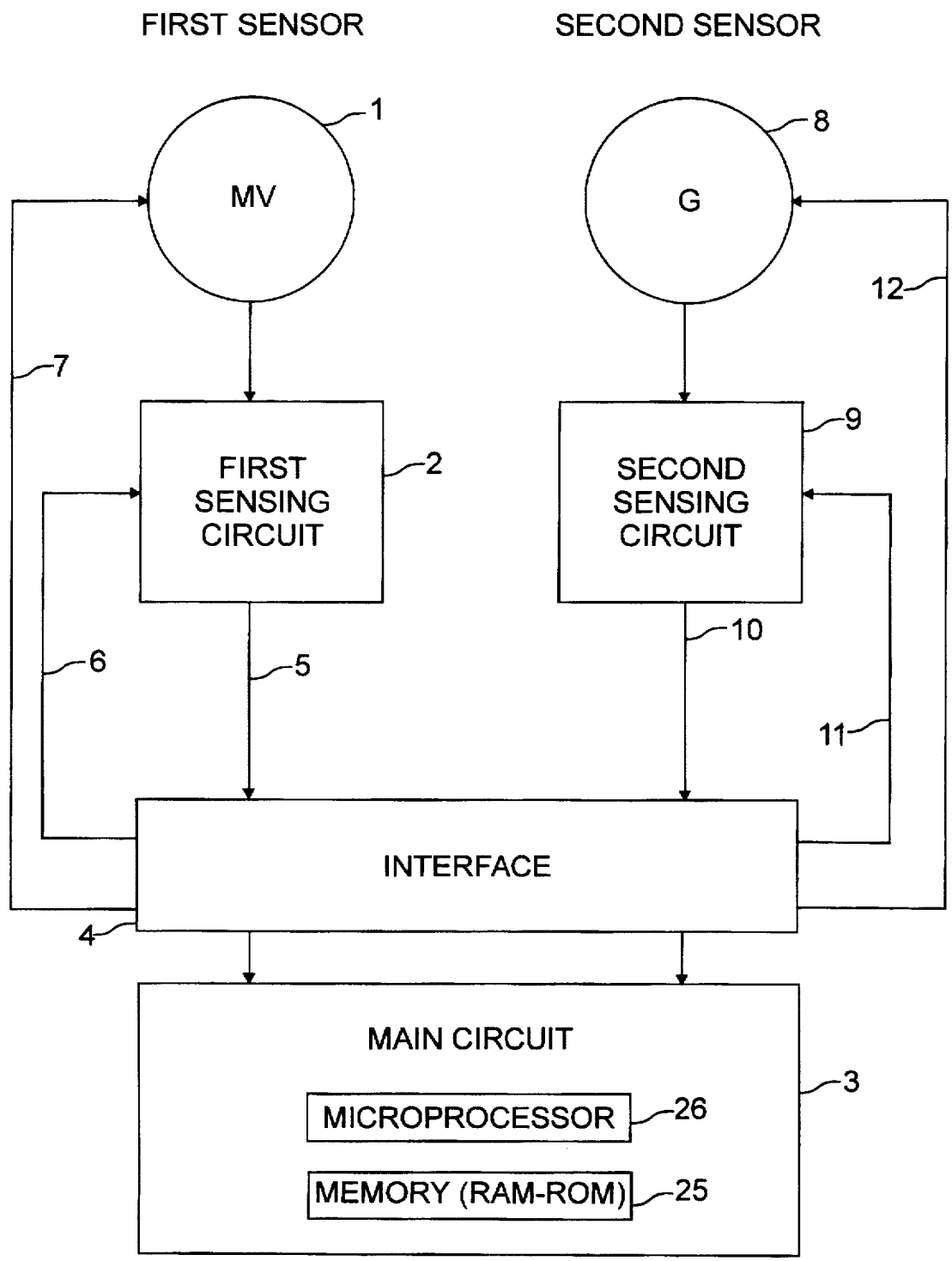

In the detailed description that follows, the invention is described in the framework of an enslaved or rate responsive cardiac pacemaker to which one or more sensors are used to control the cardiac stimulation frequency. This application is not, however, restrictive, and the teachings of this application can apply, as one will understand, to other types of active implantable medical devices having a function controlled by a sensor. Similarly, although the example refers to a pacemaker which has two sensors, a sensor of effort and a sensor of acceleration, the invention is equally applicable to a device having a single sensor of enslavement.

With reference to the schematic functional diagram of the figure, the reference 1 designates the main enslavement sensor of the pacemaker (also referred to as the "first sensor"). This first sensor 1 is associated to, that is it is coupled to, a sensing circuit 2. Sensing circuit 2 comprises substantially all of logic and hardware elements required to operate the first sensor 1 to sense the parameter and produce output signals corresponding to the sensed parameter, and to deliver a signal utilizable by the main circuit 3 of the pacemaker. Hence, in this embodiment, switching the sensing circuit out of operation also switches the first sensor out of operation. Main circuit 3 includes a microprocessor 20 and memory (RAM and/or ROM) 25, as well as conventional latches, registers and power supplies (not shown) for processing the information for the enslavement of the stimulation frequency.

In this example, the first sensor 1 is a sensor of a physiological parameter that is the "minute ventilation" (the "sensor MV"). But the invention also is equally applicable to the use of other physiological parameters, such as those previously indicated in the background of the present description; any other collection or measure of a physiological parameter that is suitable to be used for functions such as an enslavement of an active implantable device (or other function) can be substituted for the sensor MV without departing from the framework of the present invention.

The measure of the minute ventilation is in itself well known; it is described in, for example, the document "Breath-by-Breath Minute Ventilation Measurement Can Provide A Fast Response", by J. L. Bonnet, L. Kramer, M. Limousin, EUR J.C.P.E., 1994, Vol. 4, Abstract No. 329, and is commercially realized in the device sold under the trade name and model CHORUS RM 7034, manufactured by ELA Medical, Montrouge France, the assignee of the invention. Furthermore, the preferred embodiment of the process described herein is implemented in an architecture including a microprocessor 20 having associated software instructions stored in memory 25 (ROM) and analog and digital logic circuits that are themselves known. Such an architecture is, for example, employed in dual chamber cardiac pacemakers sold under the trade name CHORUS, manufactured by ELA Medical.

Although it does not present all of the advantages of the preferred solution with a microprocessor, a design in hardwired discrete circuits having dedicated logic circuits is nevertheless perfectly foreseeable, and equally within the framework of the present invention.

For a preferred implementation of the invention, one can use an interface circuit 4 (which can, in practice, be integrated as part of the main circuit 3, if necessary) for receiving output signals on lead 5 of the sensing circuit 2 in response to the sensor 1 and being able to control, respectively at leads 6 and 7, the switching in service or out of service of the sensing circuit 2 and, if necessary, of the power supply of the sensor 1 (for example, the injection of current in the case of sensor 1 providing an output signal for determining a respiration rate or a minute ventilation measure).

Advantageously, if a second sensor 8 is used, it preferably is a sensor of a non physiological parameter such as an acceleration (the "sensor G"), for example, as described in the U.S. Pat. No. 5,330,510. This sensor G comprises also a second sensing circuit 9 and delivers output signals on lead 10, transmitted via the interface circuit 4, to the main circuit 3 for use in controlling the enslavement of the stimulation. One such mode of realization with a double sensor and double enslavement allows the device to benefit from the complementary advantages of each type of sensor. The first sensor MV gives a good representation of the metabolic need of the patient, but presents a relatively long response time. The sensor G whose response time is short allows the device to detect rapidly a change of activity of the patient, and thus to detect particularly the beginning of an effort phase. One will note, however, that the difference of response time between sensors MV and G is inevitably not critically important, the sensor MV being known, for example, as sensing a physiological parameter that presents in the beginning of effort a reasonably rapid response time. Indeed, for this reason, a single enslavement to minute ventilation can, in many cases, obtain satisfactory results.

Concerning the sensor G, the interface circuit 4 can switch respectively, in 11 and 12, the placement in service or out of service the second sensing circuit 9 and the second sensor 8.

Set forth below are various implementations of the invention, for the switching in or out of service of the sensors MV and G.

In a first embodiment, which is a preferred embodiment, one uses the two sensors MV and G, and the main sensor 1 is the sensor MV. In this regard, the sensor MV controls the switching of sensor MV out of service and the sensor G controls switching sensor MV into service again.

The activity state of the sensor MV, or the patient, as the case may be, which allows one to determine if the patient is in a state of rest or a state of activity, is advantageously determined according to the manner described in the French patent 94-15912 filed 30 Dec. 1994, titled, PROCESS OF DETERMINATION OF A CRITERION OF ACTIVITY OF A SENSOR OF MEASURE OF A PARAMETER OF ENSLAVEMENT IN AN ACTIVE IMPLANTABLE MEDICAL DEVICE, in the name of ELA Medical, and the corresponding U.S. patent application Ser. No. 08/578,967 filed Dec. 27, 1995, which application is co-pending and commonly assigned, and which disclosure is incorporated herein by reference in its entirety.

Thus, the sensor MV undertakes a measure at each respiratory cycle and the sensing circuit 2 calculates a short term average at VE128 over some number, for example, 128 respiratory cycles, as well as a long term average VE24H, determined, for example, over 24 hours. Concerning the sensor G, the acceleration information is typically measured every 1.5625 second.

In this embodiment, the invention operates to switch out of service the sensor MV, more specifically the sensing circuit 2, when the sensor MV output indicates a state of rest has been established during a first predetermined duration, and to switch the sensor MV and its sensing circuit back into service if the sensor G output indicates that a non-rest state of activity has been established during a second predetermined duration. In the case of the sensor MV, the first predetermined duration may be a predetermined number of respiratory cycles, more preferably a multiple of the short term average n×VE128, where n is an integer, typically 4. In the case of sensor G, the second predetermined time may be a time duration or more preferably a number of measurement cycles, such as 32 cycles, calculated as 32×1.5625 seconds.

A general algorithm implementing this embodiment is as follows:

```
If sensor MV is in service
    all 128 respiratory cycles
        If VE128 < VE24H
            then increase (Counter__Rest__MV)
            If Counter__Rest__MV = 4
                Then switch sensor MV out of service
            otherwise nothing
        otherwise set Counter__Rest__MV = 0
otherwise [that is to say if sensor MV is out of service]
    all 4 cycles G
        If State__Sensor__G__Rest
            Then increase (Counter__Activity__G)
            If Counter__Activity__G = 8
                Then switch sensor MV in service
            otherwise nothing
        otherwise set Counter__Activity__G = 0.
```

In others words, the sensor MV (more specifically sensor 1 and its first sensing circuit 2) is switched out of service as soon as a rest phase of minute ventilation is confirmed for some period of time comprising a number of minutes; sensor MV is switched back into service again as soon as the sensor G detects a prolonged activity, with a response time on the order of 20 to 30 seconds (10 to 15 seconds to obtain reliable samples, and then four respiratory cycles thereafter to obtain the first necessary average for the enslavement to the minute ventilation parameter).

In an alternate embodiment, advantageously (but not necessarily), sensor G need not always be operating during periods of inactivity of the patient. In one implementation of this alternative, the general algorithm is as follows:

```
If State__Sensor__G = Rest
    Then
        If sensor MV is in service
            Then switch sensor G in service one of every three
                sample periods
            otherwise
                Then switch sensor G in service one of every ten
                sample periods
        otherwise
            Then switch sensor G in service all the time.
```

In other words, when the sensor MV is in service, if no activity is detected by the sensor G one turns on sensor G one cycle out of three and, as soon as an activity is suspected, one turns and leaves on sensor G. The maximal delay introduced by this implementation to detect the beginning of effort is on the order of 4.7 seconds. On the other hand, when the sensor MV is out of service (for example, during a phase of sleep), if no activity is detected by the sensor G, the sensor G is switched out of service nine out of ten cycles and, here again, as soon as an activity is suspected sensor G is turned on and left on. The maximal delay introduced by this implementation is on the order of 15.6 seconds.

In a second embodiment of the present invention, which is less advantageous but nonetheless quite suitable, the roles of sensors MV and G are reversed, with the sensor G being the main sensor (that is, the sensor 1 susceptible to switch itself out of service), and the sensor MV controlling the switching back in service of the sensor G. The aforementioned algorithms can be applied to this second embodiment without change, substituting only the MV for the G parameters and vice versa.

One will note, however, that from a physiological viewpoint, this second embodiment is less satisfactory because the time of switching into service of the sensor MV penalizes the global performance of the device. In addition, the sensor MV is the device that presents the most incremental power consumption (due to the particular fact of its functioning by an injection of current and the more complex software of the sensing circuit to determine a minute ventilation value). Therefore, it is generally preferable to put it out of service first.

Suitable sensor MV and G devices are described, for example, in the U.S. Pat. Nos. 5,299,572; 5,303,702; 5,330,510 and 5,249,572. The acceleration measure of activity also is commercially realized in the device sold under the trade name and model OPUS G 4624, manufactured by ELA Medical.

It should be understood that the invention is equally applicable to the use of any physiological or physical parameter that can be sensed or measured, and then used for functions such as an enslavement of active implantable device (and for functions other than enslavement), which can be substituted for the MV and/or G, without departing from the scope and framework of the present invention. Indeed, one skilled in the art will appreciate that the present invention can be practiced by other than the described embodiments, which are presented for purposes of illustration and not of limitation.

We claim:

1. An active implantable medical device comprising: at least one control function enslaved to a measured parameter;
   a first sensor measuring a parameter indicative of patient activity, the first sensor having an output signal corresponding to the measured parameter;
   a first sensing circuit operable to process the first sensor output signals and determine a first level of patient activity to control said at least one control function; and
   means for switching in and out of service the first sensing circuit according to the determined first level of patient activity;
wherein:
   the first sensing circuit is operable to determine when said first level of patient activity corresponds to a state of rest of the patient; and
   the switching means switches out of service the first sensing circuit in response to the first determined patient activity level corresponding to said state of rest.

2. The device of the claim 1, wherein the at least one control function further comprises a cardiac stimulation frequency, and the sensing circuit further comprises a first predetermined criteria corresponding to a calculated value of a state of rest of the patient, the device further comprising a means for determining when the first level of activity corresponds to a state of rest of a patent as a function of the first predetermined criteria and the first determined patient activity level.

3. The device of the claim 1, further comprising:
   a second sensor measuring a parameter representative of the activity of the patient and having an output signal corresponding to the measured parameter; and
   a second sensing circuit operable to process the second sensor output signals and determine a second level of patient activity.
wherein:
   the second sensing circuit is operable to determine when the determined second level of patient activity corresponds to a state of non-rest of the patient; and
   the switching means operates to switch back in service the first sensing circuit in response to the second determined patient activity level corresponding to said state of non-rest.

4. The device of the claim 1, further comprising a counter and a preselected count value, wherein the counter is incremented as a function of an elapsed time after the first sensing circuit is switched out of service, and the switching means switches back in service the first sensing circuit in response to the counter incrementing to said preselected count value.

5. The device of claim 1, in which the first sensor is a sensor of effort for measuring a parameter of physiological preponderance and delivering a signal that is a function of the effort developed by the patient.

6. The device of claim 1, wherein the first sensor further comprises a sensor for measuring an acceleration of the patient.

7. The device of claim 1, wherein the first sensor further comprises a sensor for measuring an effort of the patient.

8. The device of claim 1, wherein the first sensor further comprises a sensor for measuring a preponderantly physical parameter of the patient.

9. The device of claim 1, further comprising:
   a second sensor measuring a parameter representative of the activity of the patient and having an output signal corresponding to the measured parameter; and
   a second sensing circuit operable to process the second sensor output signals and determine a second level of patient activity.
wherein:
   the switching means operates to switch back in service the first sensing circuit as a function of the output signals delivered by the second sensor; and
   the first sensor is a sensor of effort measuring a preponderantly physiological parameter and delivering a signal that is a function of the metabolic state of the patient and the second sensor is a sensor of activity measuring a preponderantly physical parameter.

10. The device of claim 9 wherein the first sensor has a first response time, the second sensor has a second response time, and the first response time is longer than the second response time.

11. The device of claim 1, further comprising:
   a sample period;
   a second sensor measuring a parameter representative of the activity of the patient and having an output signal corresponding to the measured parameter;

a second sensing circuit operable to process the second sensor output signals over said sample period and determine a second level of patient activity selected from among at least a rest level and a non-rest level;

wherein:

the switching means operates to switch back in service the first sensing circuit in response to the determined second patient activity level corresponding to a non-rest state of the patient;

and further comprising:

means for switching in and out of service the second sensing circuit in response to the determined first patient activity level and the determined second activity level, wherein:

i) in response to the determined second patient activity level corresponding to a non-rest state, the second sensing circuit is switched in service;

ii) in response to the determined second patient activity level corresponding to a rest state and the determined first patient activity level corresponding to a non-rest state, the second sensing circuit is switched out of service for a first duration and thereafter switched in service for at least one sample period; and iii) in response to the determined second patient activity level corresponding to a rest state and the determined first patient activity level corresponding to a rest state, the second sensing circuit is switched out of service for a second duration and thereafter switched in service for at least one sample period, the second duration being longer than the first duration.

12. The device of claim 11 wherein the first duration comprises a first number of sample periods, the second duration comprises a second number of sample periods, and the second number of sample periods is greater than the first number of sample periods.

13. The device of claim 12 wherein the means for switching in and out of service the second sensing circuit further comprises a counter operable to count a first count value corresponding to said sample period, the second sensor further comprises an accelerometer sensor measuring patient motion wherein the second sensing processes the second sensor output signals periodically at a sampling interval, wherein the sample period corresponds to a first number of sampling intervals, the first number of sampling periods is a first multiple of the first number of sampling intervals, and the second number of sampling periods is a second multiple of the first number of sampling intervals.

14. The device of claim 12 wherein the means for switching in and out of service the second sensing circuit further comprises a first counter operable to count a first count value corresponding to said sample period and a second counter operable to count to a second count value corresponding to the first duration and to a third count value corresponding to the second duration, the third count value being greater than the second count value and wherein the sampling period comprises a first number of breathing cycles of the patient and the second sensor further comprises a sensor for measuring minute ventilation.

15. A method for operating a power consuming circuit of an implanted medical device having a control function enslaved to a measured parameter, comprising:

a. measuring a first parameter indicative of patient activity over a first sample period and determining therefrom a first patient activity level;

b. determining when the determined first patient activity level corresponds to a rest level of patient activity and a non-rest level of patent activity; and c. in response to a determined first patient activity level corresponding to a rest level, interrupting the measuring of the first parameter, thereby reducing power consumption during said interrupted measuring.

16. The method of claim 15 further comprising:

d. timing a period of time in response to interrupting measuring the first parameter; and e. resuming steps a–c in response to the period of time elapsing.

17. The method of claim 15 further comprising:

d. measuring a second parameter indicative of patient activity over a second sample period and determining therefrom a second patient activity level;

e. determining when said determined second patient activity corresponds to a rest level of activity and a non-rest level of activity;

f. resuming measuring of the first parameter in response to a determined second level of activity corresponding to a non-rest patient activity level.

18. The method of claim 17 wherein step a further comprises measuring a preponderantly physiological parameter and wherein step d further comprises measuring a preponderantly physical parameter.

19. The method of claim 17 wherein step a further comprises measuring a preponderantly physiological parameter indicative of the metabolic state of the patient and wherein step d further comprises measuring a preponderantly physical parameter.

20. The method of claim 17 wherein step a further comprises measuring a minute ventilation parameter and wherein step d further comprises measuring an acceleration parameter.

21. The method of claim 17 wherein step a further comprises measuring a preponderantly physical parameter and wherein step d further comprises measuring a preponderantly physiological parameter.

22. The method of claim 17 further comprising the step of counting an interval of time following each interruption of said measuring, wherein step f further comprises resuming measuring of the first parameter in response to either step e determining that the second patient activity level is non-rest or said counted interval of time, and resetting said counter in response to resuming measuring of the first parameter.

23. The method of claim 17 further comprising:

g. controlling the measuring of the second parameter by:

i) interrupting measuring the second parameter for a first duration in response to the determined first patient activity level corresponding to a non-rest level and the determined second patient activity level corresponding to a rest level, and resuming measuring the second parameter for at least one second sample period following the end of the first duration ii) interrupting measuring the second parameter for a second duration in response to the determined first patient activity level corresponding to a rest level and the determined second patient activity level corresponding to a rest level, and resuming measuring the second parameter for at least one second sample period following the end of the second duration, the second duration being longer than the first duration, and iii) maintaining measuring the second parameter in response to the determined second activity level corresponding to a non-rest level, thereby reducing power consumption during each of said first durations and said second durations.

24. The method of claim 23 wherein step g.i) further comprises providing the first duration as a first multiple of the sample period and the second duration as a second multiple of the sample period.

25. The method of claim 15 wherein step a further comprises measuring a physiological parameter representative of a minute ventilation.

* * * * *

UNITED STATES PATENT AND TRADEMARK OFFICE
CERTIFICATE OF CORRECTION

PATENT NO. : 5,766,228
DATED : June 16, 1998
INVENTOR(S) : Bonnet et al.

It is certified that error appears in the above-identified patent and that said Letters Patent is hereby corrected as shown below:

Column 1, line 60, after "one of" insert --the--;
Column 2, line 47, change "invention, concerns " to -- invention concerns--;
Column 3, line 9, change "device" to --device,--;
Column 4, line 60, change "J. C.P, E." to -- J.C.P.E.,--;
Column 6, line 7, change "every 1.5625 second" to --every 1.5625 seconds--;
Column 6, line 41, change "others" to --other--;
Column 8, line 7, change "patent" to -- patient--;
Column 10, line 52, change "first duration" to --first duration,--;

Signed and Sealed this

Fourth Day of July, 2000

Attest:

Q. TODD DICKINSON

*Attesting Officer*          *Director of Patents and Trademarks*